US008143885B2

(12) United States Patent
Chang et al.

(10) Patent No.: US 8,143,885 B2
(45) Date of Patent: Mar. 27, 2012

(54) SURFACE FLAW DETECTION AND VERIFICATION ON METAL BARS BY EDDY CURRENT TESTING AND IMAGING SYSTEM

(75) Inventors: Tzyy-Shuh Chang, Ann Arbor, MI (US); Hsun-Hau Huang, Ann Arbor, MI (US); Kazuomi Tomita, Muroran (JP); Ryuichi Seki, Muroran (JP)

(73) Assignee: OG Technologies, Inc., Ann Arbor, MI (US)

(*) Notice: Subject to any disclaimer, the term of this patent is extended or adjusted under 35 U.S.C. 154(b) by 333 days.

(21) Appl. No.: 12/606,568

(22) Filed: Oct. 27, 2009

(65) Prior Publication Data

US 2010/0109659 A1    May 6, 2010

Related U.S. Application Data

(60) Provisional application No. 61/109,774, filed on Oct. 30, 2008.

(51) Int. Cl.
*G01N 27/82* (2006.01)
*G01N 27/90* (2006.01)
*G06K 9/00* (2006.01)

(52) U.S. Cl. ........ 324/240; 324/238; 382/152; 382/141; 382/108

(58) Field of Classification Search .......... 324/234–242; 382/108, 141, 152
See application file for complete search history.

(56) References Cited

U.S. PATENT DOCUMENTS

| 4,510,447 | A | * | 4/1985 | Moyer .......................... 324/225 |
| 4,673,879 | A | | 6/1987 | Harris et al. |
| 5,006,800 | A | | 4/1991 | Hedengren et al. |
| 5,041,786 | A | * | 8/1991 | Takaishi et al. ............... 324/240 |
| 6,777,931 | B1 | | 8/2004 | Takada et al. |
| 6,850,056 | B2 | | 2/2005 | Fujisaki et al. |
| 6,950,546 | B2 | | 9/2005 | Chang et al. |
| 7,324,681 | B2 | | 1/2008 | Chang et al. |
| 7,460,703 | B2 | | 12/2008 | Chang et al. |
| 7,627,163 | B2 | | 12/2009 | Chang et al. |

FOREIGN PATENT DOCUMENTS

| JP | 2009-008659 | 1/2009 |
| JP | 2009-8659 A | 1/2009 |

* cited by examiner

*Primary Examiner* — Jay Patidar
(74) *Attorney, Agent, or Firm* — Dykema Gossett PLLC

(57) ABSTRACT

An inspection system for detecting flaws on a moving metal (e.g., steel) bar coordinates the operation of an eddy current testing (ECT)-based flaw detection apparatus and an imaging-based flaw detection apparatus. The ECT-based flaw detection apparatus and the imaging-based flaw detection apparatus are disposed along a movement path in a predetermined relationship with each other, for example, as a predetermined fixed offset distance therebetween. A synchronizing mechanism synchronizes the output data streams from the two flaw detection apparatuses based on the predetermined relationship, so as to align the data streams as function of the axial position on the metal bar. A processing unit is configured to process the synchronized data streams for the detection of flaws, which are then also synchronized (axial position). The synchronization permits a variety of cross-referencing operations, such a flaw verification as to the existence of flaws, as well augmenting imaging-based flaws with flaw depth information from the ECT-based apparatus.

11 Claims, 5 Drawing Sheets

SURFACE FLAW DETECTION AND VERIFICATION ON METAL BARS BY EDDY CURRENT TESTING AND IMAGING SYSTEM

CROSS-REFERENCE TO RELATED APPLICATIONS

This application claims the benefit of U.S. Provisional Application Ser. No. 61/109,774 filed on Oct. 30, 2008, the disclosure of which is hereby incorporated by reference in its entirety.

TECHNICAL FIELD

The present invention relates generally to a surface inspection system, and more particularly, to a non-contact, surface flaw detection system and a method of using the system to inspect elongated metal bars to detect flaws and having the ability to verify such flaw detection through cross-referencing.

BACKGROUND OF THE INVENTION

There are multiple approaches for steel bar inspection. One way is eddy current testing (ECT). Eddy current testing (ECT) has been a major approach in surface flaw detection for steel bars, for example as seen by reference to U.S. Pat. No. 6,850,056 issued to Fujisaki and Tomita entitled FLAW DETECTION DEVICE FOR STEEL BAR, hereby incorporated by reference in its entirety. ECT involves inducing an eddy current in the surface of the steel bar by way of an alternating current (AC) coil. The induced eddy current is detected using a detecting coil or the like to produce an eddy current signal. Flaws in the metal bar are detected through assessment of the magnitude and the phase of the detected eddy current signal. Another way to inspect involves use of vision or imaging systems. Vision or imaging based systems assess images taken of the steel bar for the purpose of detecting flaws or surface defects, as seen by reference to U.S. Pat. No. 7,324,681 issued to Chang et al. entitled APPARATUS AND METHOD FOR DETECTING SURFACE DEFECTS ON A WORKPIECE, SUCH AS A ROLLED/DRAWN METAL BAR, hereby incorporated by reference in its entirety. The assessment performed by image-based flaw detection may involve locating areas of contrast for example. Each flaw detection approach mentioned above, however, has its own unique characteristics.

For instance, due to the detection characteristics of ECT, it may not be able to effectively detect longitudinal types of surface flaws. Another characteristic of ECT is that it generally provides no visual feedback as to the exact nature of the detected flaw on the bar surface unless the detected locations are physically reviewed by a human being. In many primary applications, such as in hot rolling lines where bars are red hot even after inspection, or cold drawing lines where each bar could be hundreds of meters long, physical review is very difficult, if not impossible. A further characteristic of ECT, however, is that it provides some degree of depth information of the surface flaws themselves. On the other hand, one characteristic of an imaging based system is its ability to reliably detect longitudinal types of surface flaws as well as provide visual feedback as to the exact nature of the detected flaw. However, imaging-based systems in general may be limited in their ability to provide good depth information concerning detected flaws. Nonetheless, imaging based systems are known to provide near real-time, direct and intuitive visual feedback to the system operators of the detected flaws, allowing easy, although manual, flaw verification (i.e., an actual image of the flow site can be saved and made available later, which can then be used by an operator to visually verify a machine-detected flaw) and/or automatic image classification through advanced algorithms such as neural network, heuristic rules or support vector machines.

FIGS. 4A and 4B illustrate examples of a user interface for a conventional computer-based ECT data rendering system. FIG. 4A shows a screen 200, which displays a time series of the ECT data, indicated generally as ECT data 204, in an X-Y graph format, as is typical. The X-axis represents "time" and the Y-axis represents the magnitude (strength) of the ECT signal. The user interface is typically configured to allow users to preset one or more strength thresholds indicative of a detected flaw. Such thresholds may be displayed as horizontal lines, for example as indicated by reference numerals $202_L$ and $202_U$ for lower and upper threshold levels, respectively. Any ECT signal 204 that has a magnitude (strength) higher than a threshold level is considered a surface flaw detection event. For instance, when the ECT signal 204 exceeds the lower threshold level $202_L$ at location 206, the ECT rendering system considers this a surface flaw detection event. Likewise, when the ECT signal 204 exceeds the upper threshold level $202_U$ at location 208, the ECT rendering system would also consider this a surface flaw detection event. Typically, the higher the strength of the ECT signal that triggered the flaw detection event, the greater the severity of the flaw.

FIG. 4B shows a companion display to FIG. 4A. At any given moment of the ECT data 204, a corresponding phase diagram 210 may be generated and displayed by the data rendering system. In this case, a trace pattern 214 is displayed based on the phase of the detected eddy current signal (i.e., relative to the inducing signal). Just like the magnitude, the user interface provides the user with the ability to set severity thresholds, such as phase threshold 212, which are used to detect the existence of a flaw.

FIG. 5 shows an example of a user interface for a conventional computer-based image-data rendering system. A concept (not shown) may involve display of a single bar chart representing the inspected metal bar, with markings (i.e., "X") indicating at what longitudinal positions flaws have been detected. FIG. 5, on the other hand, shows a screen 300 of a user interface with a more detailed approach for displaying the inspection results. An imaging system may have multiple imaging sensors (i.e., cameras) to cover the entire circumference of the metal bar. Accordingly, the screen 300 may include a pie chart, shown in the upper left, to indicate diagrammatically the respective circumferential coverage of each one of the cameras. The screen 300 shows an extension of the single bar chart concept described above, wherein flaws (e.g., items 304, 306 marked with an "X") detected from the different image streams (i.e., different cameras) are marked on separate bar charts associated with respective cameras. This extended approach provides the user with additional circumferential information about the detection data. The screen 300 may also show (i) the direction of the movement of the metal bar, indicated by the arrow 102, as well as (ii) its speed.

With continued reference to FIG. 5, the screen 300 may also include a flaw list pane 310 which shows the inventory of the detected flaws/defects, and which may include for each flaw a variety of information, such as its respective type, size, shape and the like. The interface shown in screen 300 may also be configured to allow a user to navigate through the pane 310 and select one of the listed flaws. The interface is configured to then obtain and display more detailed information about the selected flaw. For example, the screen 300 may have a separate, additional image pane configured to display an actual image (item 302) of the metal bar inclusive of and surrounding a flaw site (item 308). Moreover, a flaw selected in pane 310 may cause its specific longitudinal position on the metal bar to be displayed on the screen 300 near the bar charts, as shown near the selected flaw 304. Notwithstanding all the information available in an image-based detection system, it would nonetheless be desirable for a user to have improved depth information concerning the detected flaws.

There is therefore a need for an inspection system that overcomes one or more of the problems or shortcoming described above.

SUMMARY OF THE INVENTION

The present invention provides a system for inspecting metal bars having the ability to (1) detect a wide variety of surface flaws, (2) provide some degree of depth information concerning such detected flaws; and (3) that includes an interface configured to provide real-time or near-real-time, direct and intuitive visual feedback and verification of such flaws.

An inspection system is provided for detecting flaws on a metal bar having an axis and moving along a movement path. The system includes a first flaw detection apparatus at a first position along the path configured to generate a first output signal indicative of eddy currents induced in the bar as it moves through the first position. The system further includes a second flaw detection apparatus at a second position along the path and disposed in a predetermined relationship with the first apparatus. The second apparatus is configured to generate a second output signal corresponding to one or more images of the bar as it moves through the second position. The system further includes a synchronizing mechanism configured to synchronize the first and second output signals as a function of an axial position of the bar based on the predetermined relationship mentioned above. Finally, the system includes a processing unit responsive to the first and second output signals for detecting first flaws and second flaws, respectively.

In a preferred embodiment, the predetermined relationship is a fixed distance separating the first (ECT) and second (imaging) flaw detection apparatuses. When the bar is moving at a known speed, a time difference (delay) can be determined between a first time when a unique position on the bar encounters the first apparatus and a second, later time when the same unique position encounters the second apparatus. The synchronizing mechanism, in a first embodiment, is configured to use a time delay circuit to insert a time delay to synchronize the first and second output signals. In a second, software-based embodiment, the synchronizing mechanism is configured to match or otherwise align the two data streams (i.e., the first and second output signals) based on the offset distance and the bar speed so that both streams are synchronized as a function of bar axial position. By synchronizing these signals, a variety of cross-reference functions can be performed, such as flaw verification, as well as augmenting the image-based detected flaw records with flaw depth information.

A combination product that includes inspected metal bar combined with a report describing the inspection results (in electronic form) is also presented.

BRIEF DESCRIPTION OF THE DRAWINGS

The present invention will now be described by way of example, with reference to the accompanying drawings.

DETAILED DESCRIPTION OF THE PREFERRED EMBODIMENT

Figure 1:
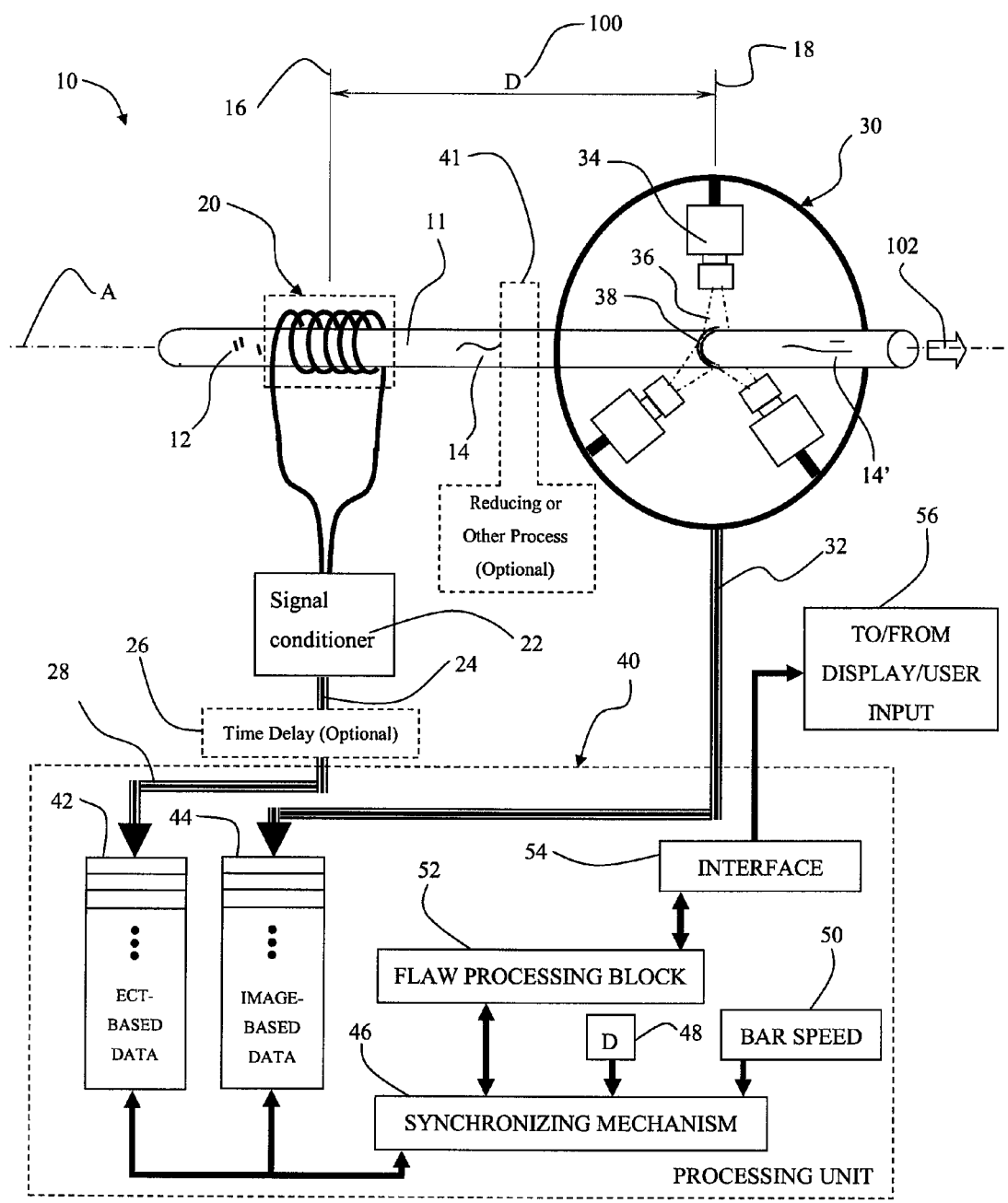
FIG. 1 is a diagrammatic and block diagram of an inspection system according to the invention having among other features a synchronizing mechanism.

Referring now to the drawings wherein like reference numerals are used to identify identical components in the various views, FIG. 1 is a diagrammatic and block diagram of an inspection system 10 according to the invention. The system 10 includes functionality configured to allow coordination of both eddy current testing based and image-based inspection devices where their outputs, showing detected flaws, may be synchronized. Through the foregoing, many advantages may be achieved, including the ability (i) to cross-reference flaw detections between both inspection devices for verification purposes; (ii) to use an ECT-based flaw detection as a trigger to capture an image; (iii) to augment image-based surface flaw detection results with flaw depth information provided by eddy current testing (ECT) inspection device.

With continued reference to FIG. 1, the system 10 is configured to inspect a metal bar 11 having a longitudinal axis designated "A". The system 10 is configured to inspect the metal bar 11 for surface flaws as the metal bar 11 moves along a movement path. Preferably, the axis "A" of the metal bar 11 is substantially coincident with the movement path, and at least in the area proximate the inspection system, comprises a linear movement path. In one embodiment, the metal bar 11 may be a hot, steel bar of the type produced in a steel mill, as described in more detail in U.S. Pat. No. 7,324,681 issued to Chang et al. entitled APPARATUS AND METHOD FOR DETECTING SURFACE DEFECTS ON A WORKPIECE, SUCH AS A ROLLED/DRAWN METAL BAR, hereby incorporated by reference in its entirety. The bar 11 may include various types of surface flaws or defects, such as transverse oriented flaws 12 as well as longitudinal oriented flaws 14 and 14'.

The inspection system 10 includes a first flaw detection apparatus, such as an eddy current testing (ECT) apparatus 20 and a second flaw detection apparatus, such as an imaging-based apparatus 30. The first (ECT) apparatus 20 is disposed at a first axial position 16 along the movement path, while the second apparatus 30 is disposed at a second axial position 18 along the path. Generally, the second apparatus 30 is in a predetermined relationship with the first apparatus 20. In a preferred embodiment, the predetermined relationship may be a fixed, axial distance. Thus, the second axial position 18 may be offset from the first axial position by a predetermined distance 100 (also designated "D" in FIG. 1) as taken along the movement path. The bar 11 is arranged, relative to the inspection system 10, so as to be inspected by both the first (ECT) apparatus 20 and the second (imaging) apparatus 30. In accordance with the present invention, the two apparatus 20, 30 are linked, as described in greater detail below, such that the data output from the two apparatuses are synchronized with respect to the axial position on the bar 11. In addition, provided the bar 11 is moving at a known speed, which is typically the case, such synchronization may be time-based as well.

Figure 4A:
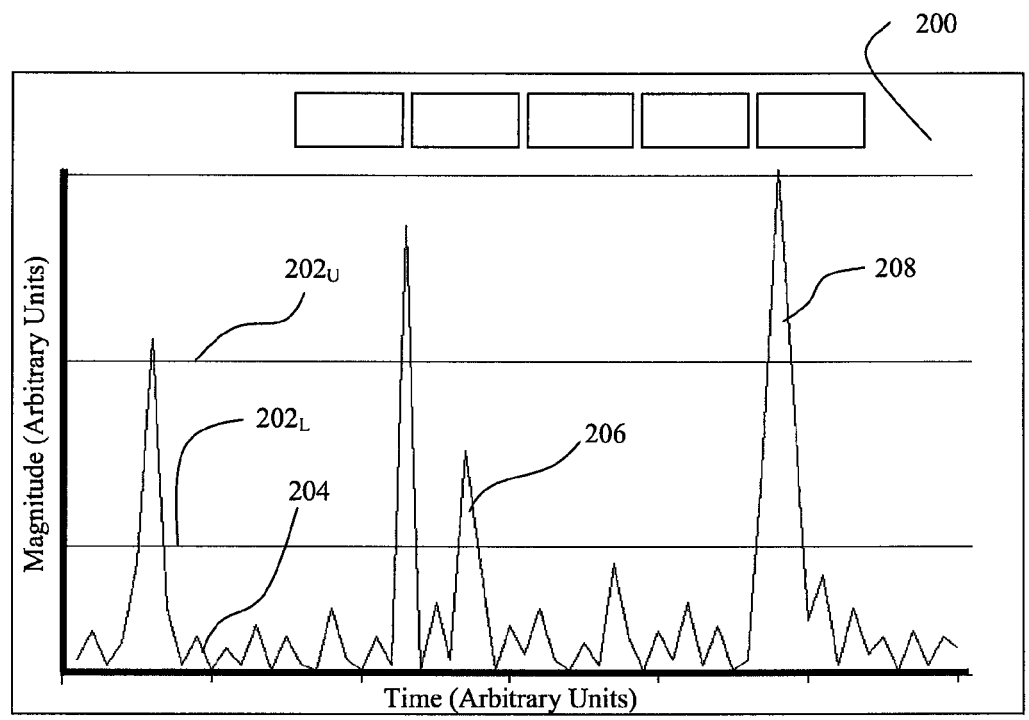
FIGS. 4A-4B are screen displays showing magnitude and phase components of a conventional ECT data rendering device.
Figure 4B:
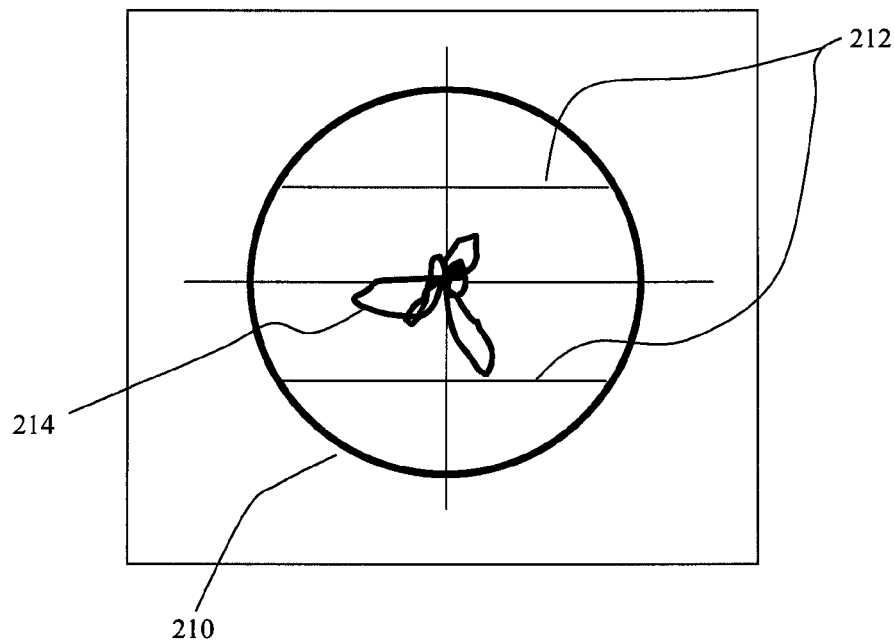

With continued reference to FIG. 1, the first (ECT) apparatus 20 is configured to generate a first output signal 24 corresponding to an eddy current induced in the bar 11 as it moves through the first axial position 16. The first (ECT) apparatus 20 may comprise conventional components known in the art for conducting eddy current testing (ECT)-based metal bar flaw detection. In this regard, U.S. Pat. No. 6,850,056 issued to Fujisaki and Tomita entitled FLAW DETECTION DEVICE FOR STEEL BAR is hereby incorporated by reference in its entirety. Note, although FIG. 1 shows a diagrammatic depiction of a only a detection coil, it should be understood that other structure, such as one or more AC inducing coils, guide sleeves and the like may also be present to perform the eddy current testing as known in the art. FIG. 1 further shows a signal conditioning block 22 configured to interact with the detection coil to produce the first output signal 24. The first output signal 24 contains information regarding the eddy currents induced in the surface of the metal bar 11, and which may be processed in accordance with conventional approaches to obtain magnitude and phase values, which as described above in connection with FIGS. 4A and 4B may be used to detect flaws. The first output signal 24 therefore includes, and thus may be processed to extract, information indicative of the depth and/or severity of a surface flaw.

The second (imaging)-based apparatus 30 is configured to generate a second output signal 32 corresponding to one or more images of the surface of the bar 11 as it moves through the second axial position 18. In the illustrative embodiment, each one of a plurality of image acquisition means (e.g., line scan cameras) may have a respective field of view 36, which when combined together allow image capture of the entire circumference 38 of the metal bar 11. Thus, as the bar 11 moves axially, the entire surface thereof may be inspected for flaws. The inspection apparatus 30 may further include suitable illumination mechanisms (not shown) as well as suitable control mechanisms (not shown), as known in the art. Thus, the second (imaging) apparatus 30 may generally comprise conventional components known in the art for conducting imaging-based flaw detection of moving metal bars. In this regard, U.S. Pat. No. 7,324,681 issued to Chang et al. entitled APPARATUS AND METHOD FOR DETECTING SURFACE DEFECTS ON A WORKPIECE, SUCH AS A ROLLED/DRAWN METAL BAR is hereby incorporated by reference in its entirety.

The system 10 further includes a processing unit 40 responsive to the first output signal (i.e., signal 24) from the first apparatus 20 for detecting one or more first flaws. The processing unit 40 is further responsive to the second output signal (i.e., signal 32) from the second apparatus 30 for detecting one or more second flaws. The processing unit 40 may comprise conventional processing structure known in the art, such as but not limited to a digital computer, an analog computer or equivalent processing devices such as a digital signal processor (DSP), a field programmable gate array (FPGA) and other equivalents now known or hereafter developed. Preferably, the processing unit 40 is configured via suitable programming to contain various software algorithms to perform the functions described herein. In this regard, the processing unit 40 may include at least one, and optionally multiple, microprocessor or other processing units, associated memory devices such as read only memory (ROM) and random access memory (RAM), and various input and output interface devices. The software algorithms which are executed in the processing unit 40 may generally comprise conventional strategies known to those of ordinary skill in the art, subject to the additional synchronization and related functionality described herein for coordinating and cross-referencing the output signals of the first and second apparatuses 20, 30. Such software algorithms are preferably embodied in pre-programmed data stored for use by the processing unit 40.

The system 10 further includes a synchronizing mechanism configured to synchronize the first (ECT) output signal 24 and the second (imaging) output signal 32 as a function of an axial position on the metal bar, based on the predetermined relationship between the first and second apparatuses 20, 30. Such a predetermined relationship could be in any form that those skilled in the art could understand. In the illustrated embodiment, as described above the fixed, predetermined distance 100 ("D") between the first (ECT) and second (imaging) apparatuses 20, 30 is used to establish the relationship, wherein the synchronizing mechanism is specifically configured to compensate for the timing differences between signals 24, 32 as a result of the predetermined offset distance 100 ("D"). However, it should be understood that other predetermined relationships are possible. For example, it may be possible that between the first (ECT) apparatus 20 and the second (imaging) apparatus 30, the bar 11 could be mechanically processed. For instance, there could be a mill set 41 or the like between the two apparatuses configured to reduce the cross-section of the bar 11. Such a mechanical process as effected by device 41 would cause the bar 11 to deform in shape. In such a case, the predetermined relationship between the first (ECT) and second (imaging) apparatuses would also describe the deformation and the resulting enlargement of the axial length in such a way that unique positions can still be correlated as inspected by the two apparatuses. Such a predetermined relationship could also be accurately described and be implemented in the synchronizing mechanism.

The synchronizing mechanism, in a first embodiment, may be implemented using hardware (e.g., electronics) and in a second embodiment, may be implemented in software executing on the processing unit 40.

In the first embodiment, the synchronizing mechanism may take the form of a time delay block 26 configured to insert a predetermined time delay between its input and output. In the illustrated set-up, the first (ECT) output signal 24 is delayed by this predetermined amount thereby producing a delaying (synchronized) first (ECT) output signal 28. A number of factors may be used to calculate the predetermined time, including (i) the relationship between the inspection apparatuses 20, 30, (ii) in particular the distance 100 ("D") (iii) and a speed parameter indicative of the speed at which the metal bar 11 moves along the movement path. The predetermined time delay is thus the time difference between (i) a first time when a unique location on the bar 11 is inspected by the first (ECT) apparatus 20 and (ii) a second time, subsequent to the first time, when the same unique location on the bar 11 is inspected by the second (imaging) apparatus 30. The foregoing assumes movement of the bar 11 in the direction 102 (FIG. 1), and the particular orientation of the first apparatus 20 relative to the second apparatus 30 (i.e., ECT first, then imaging-based. On the other hand, if the second (imaging) apparatus 30 is installed to inspect the bar 11 first, then the time delay block 26 will be set-up to delay the second (imaging) output signal 32 instead.

The second embodiment of the synchronizing mechanism involves the use of software to synchronize the output signals 24, 32 of the two apparatuses 20, 30. As shown in FIG. 1, the system 10 may include a first data structure 42 having a first data set corresponding to the first (ECT) output signal 24. The first data structure 42, in the illustrative embodiment, may be populated with ECT data by converting (e.g., digitizing at a desired sampling rate/depth) the first (ECT) output signal 24 into the first data set of digital data, and then storing the first (ECT) data set in the data structure 42. The data structure 42 may be formed in any storage medium, including RAM, hard drive or the like. Likewise, the system 10 may further include a second data structure 44 having a second data set corresponding to the second (imaging) output signal 32. The second data structure 44, in the illustrative embodiment, may be populated with imaging data by converting (e.g., digitizing, if necessary) the second output signal 32 and storing the second (imaging) data set in the data structure 44. The second data structure 44 may also be formed in any storage medium, including RAM, hard drive or the like. It should be appreciated that for many commercially available imaging devices (cameras), the output signal may already be in digital form and need not have to be digitized. Nonetheless, at least some conversion may be needed and/or at least desirable to reconcile various aspects of the first and second signals 24, 32.

To achieve the desired synchronization, the processing unit 40 includes a synchronizing mechanism 46 configured via suitable software, or hardware derived from a set of software codes, running in the processing unit 40, arranged to match the first data set in the first data structure 42 with the second data set in the second data structure 44 (i.e., to match the two signal streams originating from the ECT-based and imaging-based flaw detection apparatuses). The synchronizing mechanism 46 may be further configured to perform the matching as a function of the axial position on the metal bar 11, based, in the illustrative embodiment, on both (i) the predetermined distance D, shown as an input parameter 48 and (ii) the bar speed 50. As the software embodiment provides an improved measure of flexibility for adjustment and in the ease of implementing complex relationships (if present) between the two apparatuses 20, 30, it is a preferred implementation.

The processing unit 40 may also include a flaw processing block 52 and a user interface 54. It should be appreciated that the user interface 54 may be implemented as a separate block (i.e., data rendering software) suitable for execution on the same or a separate processing unit 40.

The flaw processing block 52 may be generally responsive, in the preferred software embodiment, to both the first (ECT) data set in the first data structure 42 and the second (imaging) data set in the second data structure 44 for detecting first (ECT) flaws and second (imaging) flaws. Conventional strategies, based on the respective data sets, may be used to implement detection of such flaws. The interface 54 is configured to interact with a display unit and/or user input 56 to display where the first flaws from the first (ECT) apparatus 20 and the second flaws from the second (imaging) apparatus 30 are located with respect to an axial position on the metal bar 11. An exemplary screen display produced by the interface 54 will be described in connection with FIG. 3.

Figure 2:
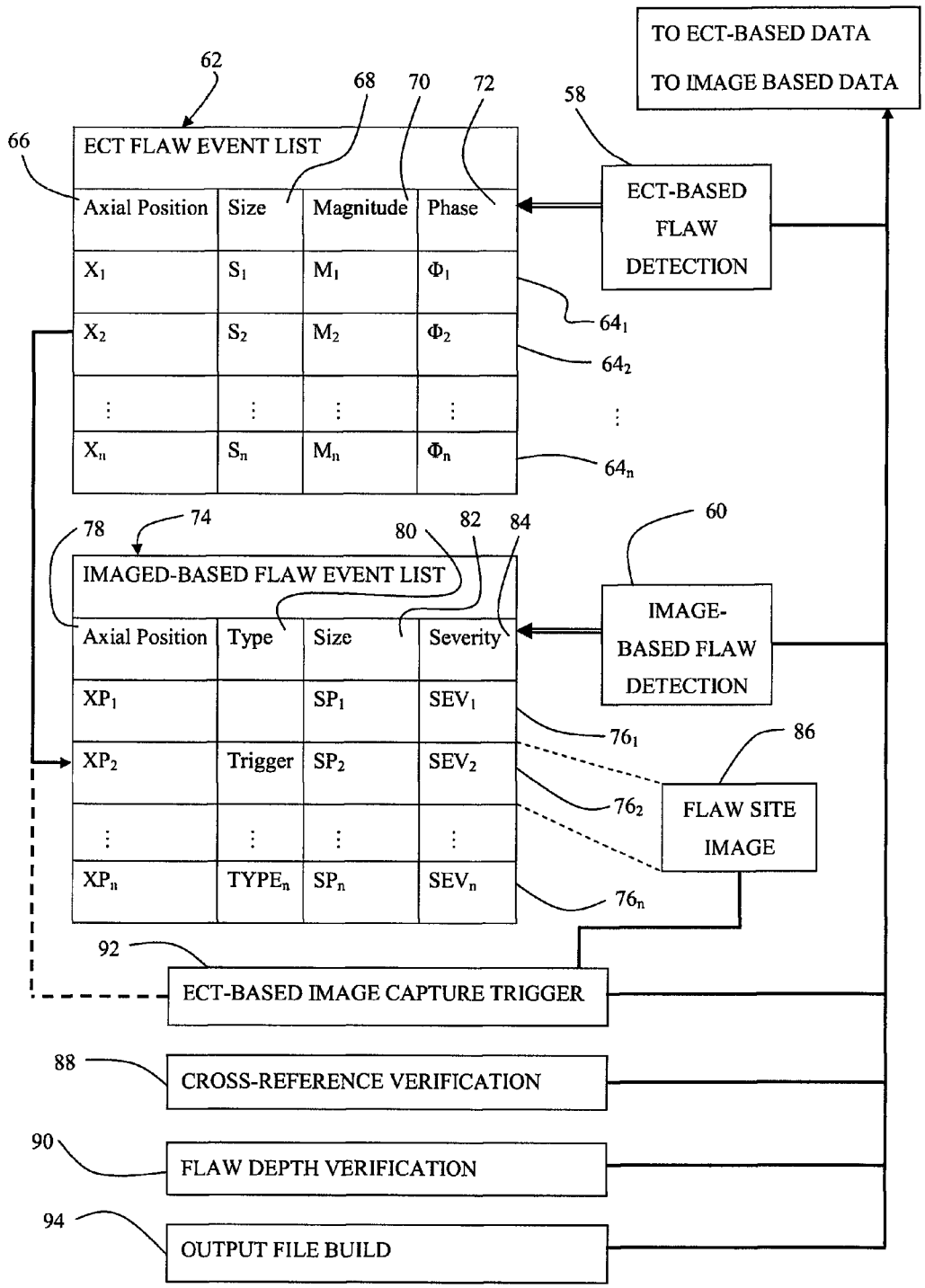
FIG. 2 is a simplified block diagram showing, in greater detail, a flaw processing block.

FIG. 2 is a simplified block diagram showing, in greater detail, the flaw processing block 52 of FIG. 1. The flaw processing block 52 may include an ECT-based flaw detection block 58 and an image-based flaw detection block 60.

The ECT-based flaw detection block 58 is responsive to the ECT-based data contained in the data structure 42 for detecting surface flaws of the metal bar 11, which collectively define a set of first flaws. The set of first flaws may be arranged and stored in a flaw detection event list 62 having a plurality of information records $64_1, 64_2, \ldots, 64_n$ corresponding to the detected flaws. Each information record $64_i$ where i=1 to n, may be related to one flaw and may itself have a plurality of fields, and which, for example only, may include an axial position field 66 (where the flaw is located), a flaw size field 68, a magnitude field 70 and a phase field 72. The ECT-based flaw detection block 58 may comprise conventional structures and conventional strategies for detecting flaws via the processing of eddy current testing (ECT) data. For example, various magnitude and phase thresholds, as described above in connection with FIGS. 4A and 4B, may be used to determine the existence and depth/severity of a flaw. In a preferred embodiment, the detection strategy may be implemented in accordance with programmed algorithms executing on the processing unit 40. It should be appreciated that the magnitude and phase values for any particular detected flaw provide flaw depth information, as known to one of ordinary skill in the art.

Likewise, the image-based flaw detection block 60 is responsive to the image-based data contained in the data structure 44 for detecting surface flaws of the metal bar 11, which collectively define a set of second flaws. The set of second flaws may be arranged and stored in a flaw detection event list 74 having a plurality of information records $76_1, 76_2, \ldots, 76_n$ corresponding to the detected flaws. Each information record $76_i$ where i=1 to n, may be related to one flaw and may itself have a plurality of fields, and which for example only, may include an axial position field 78 (where the flaw is located), a type field 80, a flaw size field 82 and a flaw severity field 84. In addition, each information record $76_i$ may further include one or more images 86 of (and surrounding) the respective flaw site. The image-based detection block 60 may comprise conventional structures and conventional strategy for detecting flaws according to and based on image data. While such algorithms are known in the art, such algorithms may be described generally as including a first layer of processing involving comparison of local contrast in the image, such as by comparing a first predetermined threshold to the local contrast. A second layer of processing may involve applying a second predetermined threshold to detect the nature of the defect such as size, location, length, width and the like. A more complete description of just one exemplary approach may be found by reference to U.S. Pat. No. 7,324,681 incorporated by reference above. In one embodiment, the detection methodology is implemented in accordance with programmed algorithms executing on the processing unit 40.

It should be appreciated that the axial position fields 66 and 78 in the lists 62, 74 are synchronized with respect to an axial position on the metal bar 11 by virtue of the synchronizing mechanism 46 in FIG. 1. That is, the same axial position values in each of the fields 66, 78 will point to the same, unique location on the metal bar 11. Also, it should be understood that while two separate lists 62, 74 are illustrated for simplicity's sake, a consolidated list or structure (not shown) may be used as well, as understood by one in the art.

With continued reference to FIG. 2, the processing unit 40 includes further functional blocks configured to provide enhanced capability. Specifically, the processing unit 40 may include means 88 for cross-referencing the first and second sets of flaws (or a flaw within a set), one with the other. The general function of cross-referencing flaw data from the two lists 62, 74 permits various forms of verification, thereby providing for improved integrity of the final flaw list. For example, the cross-referencing means 88 may include a mechanism configured to verify, for a subject flaw in one of the flaw lists 62, 74, the existence of a corresponding flaw at substantially the same axial position in the other, non-selected flaw list 62, 74. It should be appreciated that location, size, etc. need not appear to be exact in both lists 62, 74; however, suitable tolerances may be established, based on the known accuracy or resolving capability for each of the flaw detection apparatuses 20, 30.

The cross-referencing means 88 may further include a mechanism configured to augment, for at least one of the flaws in the flaw list 74, the related information record 76 by including one or more flaw depth parameters taken or derived from the ECT-based flaw list 62. In other words, since the identified flaws in each of the ECT-based flaw list 62 and the image-based flaw list 74 are synchronized as a function of axial position on the metal bar 11, the flaw depth information (e.g., magnitude and phase) for a particular flaw in list 62 can be carried forward and/or otherwise associated with the same flaw in the list 74 (this is best shown graphically in FIG. 3). This can be accomplished by virtue of the common frame of reference found in each list (i.e., the axial position).

In addition, the processing unit 40 may still further include an ECT-based image capture mechanism (block 92) configured to capture an image of the metal bar 11 inclusive of and surrounding an ECT-detected flaw when the ECT-based flaw is detected. The image capture mechanism 92 may be configured to perform this function by extracting the desired image or images from the second output signal 32 produced by the image-based apparatus 30. This may be performed, for example, by identifying the appropriate segment of data to extract from the second data structure 44. Note that the first (ECT) and second (imaging) output signals are synchronized as to axial position, at least insofar as the digitized information contained in the respective data structures 42, 44 are concerned. Accordingly, the axial position of the ECT-flaw can be used as a pointer of sorts into the image-based data structure to identify the appropriate image data. In addition, it should be understood that the image capture mechanism 92 can be triggered by an ECT-based flaw detection event independent of whether the second (image-based) flaw detection apparatus 30 actually detects a flaw at substantially that same axial location. For example, an eddy-current flaw detection event may cause a signal to be produced, which, if longer than a predetermined time (e.g., 40 milliseconds), will be interpreted as satisfying a trigger condition, making the ECT flaw detect event viewable. In this way, an image of the site may be retained for later evaluation.

The processing unit 40 may still further include an output file build block 94 configured to generate an output file (i.e., a record in electronic form) containing the results of the inspection performed by system 10 (e.g., the flaw lists 62, 74) and may further include an actual image of the site of the detected flaw (and surrounding area). The output file (electronic record) is contemplated to be provided with the inspected metal bar 11 and may be configured for use by a customer of such a combination product (i.e., the customer of inspected metal bar also gets the electronic record containing the inspection results). In this regard, various features of the user interface 54 to be described below may be implemented in a separate data rendering software for use by the customer on his computer.

Figure 3:
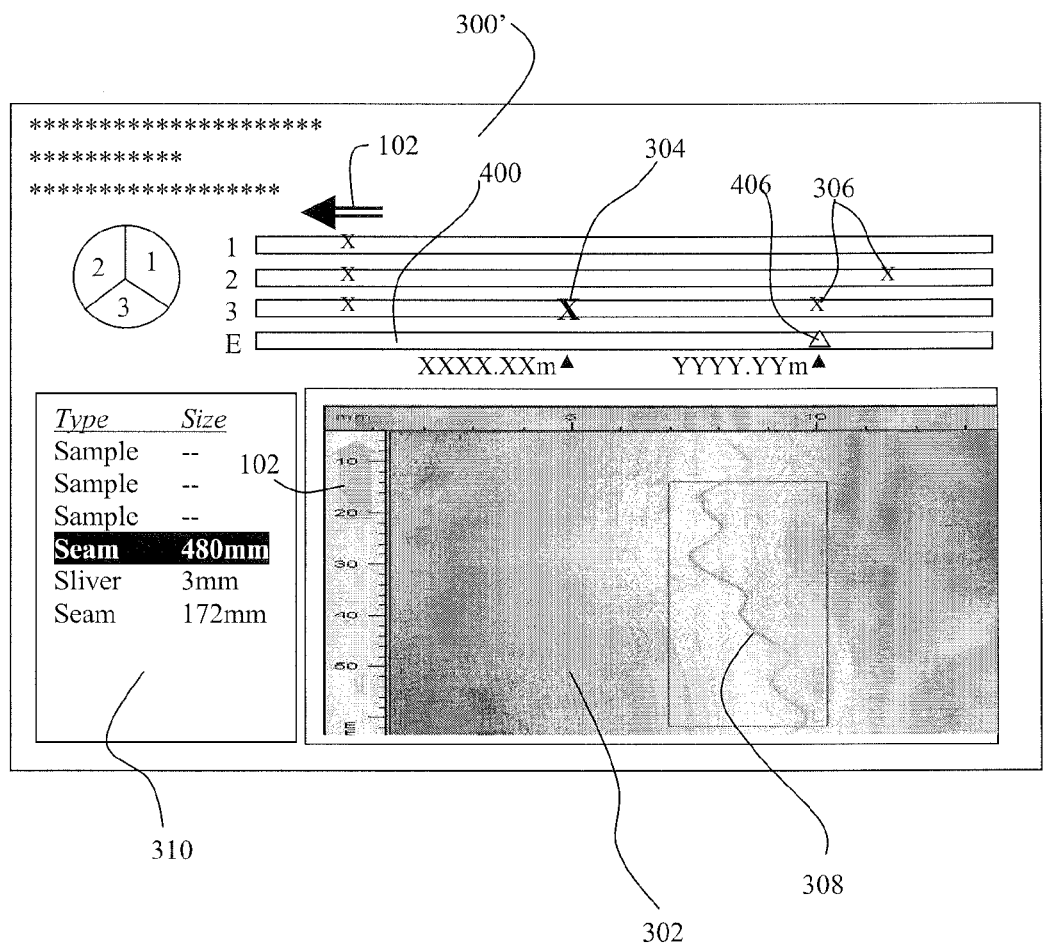
FIG. 3 is a simplified screen display showing the results of the inspection system of FIG. 1, where image-based and ECT-based flaws are shown on the same bar chart depiction of the metal bar.
Figure 5:
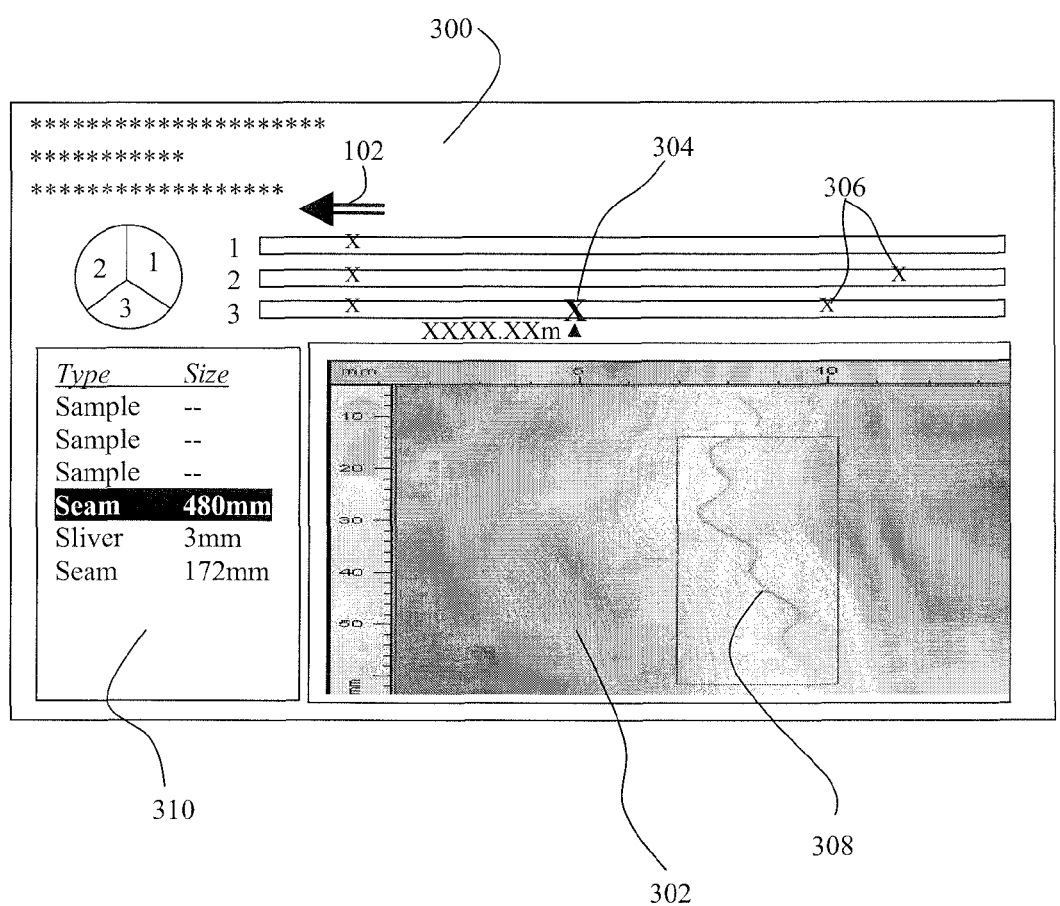
FIG. 5 is a screen display showing detected surface flaws of a conventional image-based inspection data rendering device software.

FIG. 3 is a simplified screen display showing the results of the inspection system of FIG. 1. FIG. 3 shows a screen display 300', which is substantially the same as that shown and described in connection with FIG. 5, but which includes the following additions. First, a diagrammatic depiction, designated 400, of the metal bar 11 has been added, and functions to display ECT-based flaws at various axial positions on the bar. Bar chart 400 is distinguished from the other bar chart depictions by the letter "E" at the far left thereof. Symbol 406 denotes a flaw detected by the ECT flaw detection apparatus 20, which is synchronized to the common axial position as with the image-based detected flaws (e.g., 304, 306). Moreover, a plurality of different symbols may be used for the ECT-based flaws, each indicating a respective, differing severity/depth associated with that flaw.

Those skilled in the art will also appreciate that the synchronized data from the two different devices can be used for various purposes such as cross-referencing. Those skilled in the art shall also appreciate that if the two devices are substantially synchronized in real-time, it is possible for one device to trigger another one for the same location signal recording. For instance, if the ECT detects an event, the event may trigger the imaging system to store the image(s) of the location of detection for review, whether or not the imaging device detects any anomalies at the same location. Those skilled in the art will appreciate that the method to synchronize the ECT and imaging devices can also be expanded to take in other data such as the temperature history of the metal bar as it passes through the inspection device.

It should be understood that the functional and other descriptions and accompanying illustrations contained herein will enable one of ordinary skill in the art to practice the inventions herein without undue experimentation. It is contemplated that the invention will preferably be practiced through programmed operation (i.e., execution of software computer programs) of the processing unit 40.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law

The invention claimed is:

1. An inspection system for detecting flaws on a metal bar having an axis moving along a movement path, comprising:
a first flaw detection apparatus at a first position along said path configured to generate a first output signal indicative of eddy currents induced in said bar as it moves through said first position;
a second flaw detection apparatus at a second position along said path and disposed in a predetermined relationship with said first apparatus, said second apparatus being configured to generate a second output signal corresponding to one or more images of said bar as it moves through said second position;
a synchronizing mechanism configured to synchronize said first and second output signals as a function of an axial position of said bar based on said predetermined relationship;
a processing unit responsive to said first and second output signals for detecting first flaws and second flaws, respectively, and cross-referencing a selected one of the said first and second output signals with another one of the said first and second output signals.

2. The system of claim 1 wherein the metal bar moves in a first direction such that a unique location on said bar encounters said first flaw detection apparatus at a first time and said second flaw detection apparatus at a second time subsequent to said first time, said predetermined relationship comprising a predetermined offset distance between said first and second flaw detection apparatuses, and
wherein said synchronizing mechanism comprises a time delay device configured to delay said first output signal by a predetermined time so as to compensate for said offset of said predetermined distance.

3. The system of claim 2 wherein said predetermined time is determined as a function of (i) said offset of said predetermined distance between the first and second flaw detection apparatuses and (ii) a speed parameter indicative of the speed at which the metal bar moves along said path.

4. The system of claim 1 wherein the metal bar moves in a first direction such that a unique location on the metal bar encounters said first flaw detection apparatus at a first time and said second flaw detection apparatus at a second time subsequent to said first time, said system further comprising:
(i) a first data structure having a first data set corresponding to said first output signal;
(ii) a second data structure having a second data set corresponding to said second output signal; and
wherein said synchronizing mechanism includes means for matching said first data set with said second data set as a function of axial position of the metal bar based on said predetermined relationship.

5. The system of claim 1 wherein said cross-referencing means includes a mechanism configured to verify, for a subject flaw from the selected set of flaws, the existence of a corresponding flaw at substantially the same axial position in the non-selected set of flaws.

6. The system of claim 1 wherein said selected set is said set of second flaws, said cross-referencing means including a mechanism configured to augment, for at least one of said second flaws, a respective information record associated therewith by including a flaw depth parameter derived from said first flaw detection apparatus.

7. The system of claim 1 wherein said selected set is said set of first flaws, said cross-referencing means including a mechanism configured to augment, for at least one of said first flaws, a respective information record associated therewith by including an image and the associated image features for at least one of a size, a shape, a contrast level of the detection derived from said second flaw detection apparatus.

8. An inspection system for detecting flaws on a metal bar having a longitudinal axis moving along a movement path, comprising:
a first flaw detection apparatus disposed at a first position along said path configured to generate a first output signal corresponding to an eddy current induced in the metal bar as it moves through said first position;
a second flaw detection apparatus disposed at a second position along said path, said second position being offset from said first position by a predetermined distance along said path, said second flaw detection apparatus being configured to generate a second output signal corresponding to image data of a surface of said metal bar as it moves through said second position;
a processing unit responsive to said first output signal for detecting first flaws and further responsive to said second output signal for detecting second flaws;
a synchronizing mechanism configured to synchronize said second output signal with said first output signal as a function of an axial position of the metal bar so as to compensate for said offset of said predetermined distance wherein said first flaws and said second flaws have respective axial positions that are synchronized with respect to the metal bar.

9. A combination product comprising:
(i) a steel bar that has been inspected for flaws by an inspection system, and (ii) a record in electronic form created by the inspection system describing the results of the inspection of said steel bar, said record including, for each detected flaw:
a respective location of each detected flaw relative to a start position on the bar;
a respective notation of the nature of the flaw comprising at least one of a size, a shape, a contrast level and a flaw depth; and
wherein said inspection system is configured for inspecting said bar wherein said bar is elongated and extends and moves along a longitudinal axis in a manufacturing process, said inspection system including:
a first flaw detection apparatus disposed at a first position along said path configured to generate a first output signal corresponding to an eddy current induced in the metal bar as it moves through said first position;
a second flaw detection apparatus disposed at a second position along said path, said second position being offset from said first position by a predetermined distance along said path, said second flaw detection apparatus being configured to generate a second output signal corresponding to image data of a surface of said metal bar as it moves through said second position;
a synchronizing mechanism configured to synchronize said second output signal with said first output signal as a function of an axial position of the metal bar so as to compensate for said offset of said predetermined distance; and
a processing unit responsive to said first output signal for detecting first flaws and further responsive to said second output signal for detecting second flaws, said first flaws and said second flaws having respective axial positions associated therewith that are synchronized with respect to the metal bar.

10. The product of claim 9 wherein said record further includes an actual image of the site of and surrounding the detected flaw.

11. The product of claim 10 wherein said record is configured for use by a customer of said product.

* * * * *